(12) United States Patent
Bengmark

(10) Patent No.: US 7,201,738 B1
(45) Date of Patent: Apr. 10, 2007

(54) CATHETER FOR PROVIDING A FLUID CONNECTION WITH THE SMALL INTESTINE

(75) Inventor: Stig Bengmark, Lund (SE)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 09/355,665

(22) PCT Filed: Feb. 2, 1998

(86) PCT No.: PCT/SE98/00145

§ 371 (c)(1),
(2), (4) Date: Sep. 17, 1999

(87) PCT Pub. No.: WO98/33469

PCT Pub. Date: Aug. 6, 1998

(30) Foreign Application Priority Data

Feb. 4, 1997 (SE) .................................. 9700373

(51) Int. Cl.
*A61M 5/178* (2006.01)
(52) U.S. Cl. ............... 604/170.03; 604/270; 604/910
(58) Field of Classification Search ............... 604/48, 604/93.01, 104, 164.01, 170.02, 170.03, 604/174–175, 264, 270, 523, 528, 537, 539, 604/910; 606/191, 198; 623/23.64, 23.65
See application file for complete search history.

(56) References Cited

U.S. PATENT DOCUMENTS

| | | | | |
|---|---|---|---|---|
| 3,399,668 A | * | 9/1968 | Lundgren | .................. 600/435 |
| 4,834,724 A | * | 5/1989 | Geiss et al. | .................. 604/540 |
| 4,887,996 A | | 12/1989 | Bengmark | |
| 5,059,169 A | | 10/1991 | Zilber | ............................ 604/8 |
| 5,256,146 A | * | 10/1993 | Ensminger et al. | ......... 604/104 |
| 5,601,537 A | | 2/1997 | Frassica | ...................... 604/264 |
| 5,902,285 A | | 5/1999 | Kudsk et al. | |
| 5,984,896 A | * | 11/1999 | Boyd | ......................... 604/175 |
| 6,280,434 B1 | * | 8/2001 | Kinoshita et al. | ........... 604/530 |
| 6,344,038 B1 | * | 2/2002 | Weber | ........................... 606/1 |
| 6,743,198 B1 | * | 6/2004 | Tihon | ......................... 604/104 |
| 2005/0245846 A1 | * | 11/2005 | Casey | ........................ 600/585 |

FOREIGN PATENT DOCUMENTS

EP 0278937 8/1998

* cited by examiner

*Primary Examiner*—LoAn H. Thanh

(57) ABSTRACT

Probe for providing a fluid connection with the small intestine comprising a tube (10) to be inserted in the small intestine via the stomach, having proximal and distal open ends (10A, 10B) and inherent tendency of coiling over a predetermined length at the distal end, and a guide (14) displaceable in the tube from the proximal end for straightening said length in order that it shall be straightened during the actual insertion into the stomach. According to the invention the tube has at least in said predetermined portion a hairy, frosted, rough, ribbed or finned outside surface (16).

22 Claims, 2 Drawing Sheets

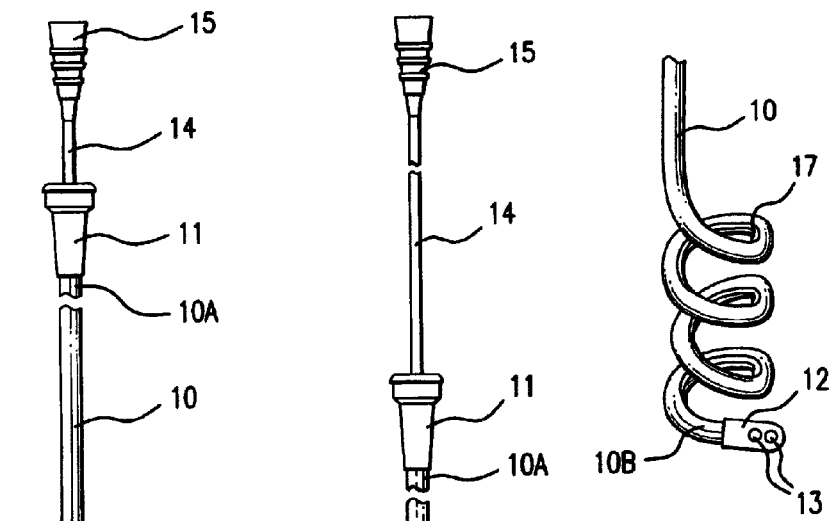
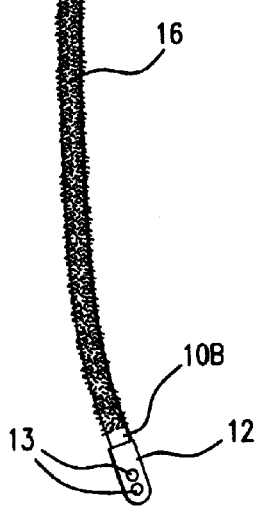
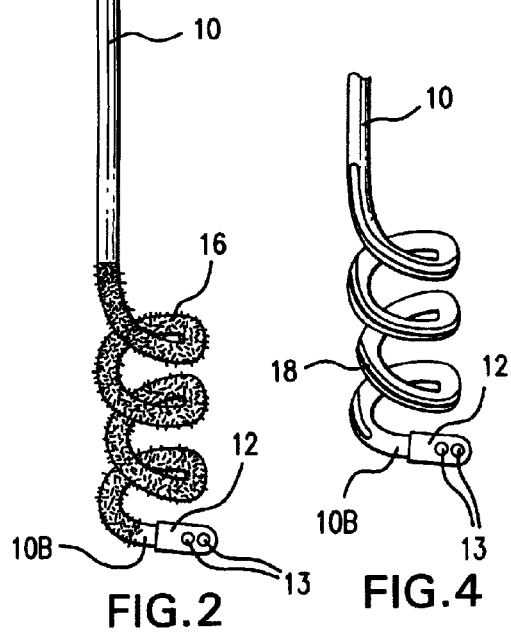
FIG. 1    FIG. 2    FIG. 3    FIG. 4

CATHETER FOR PROVIDING A FLUID CONNECTION WITH THE SMALL INTESTINE

BACKGROUND ART

The invention relates to a catheter for providing a fluid connection with the small intestine, preferably for liquid supply, for example nutriment supply, to said intestine but also for diagnostics (injection of contrast agent for taking an X-ray of an intestine or taking samples of the testine contents or the mucous membrane), comprising a tube to be inserted into the small intestine via the stomach, having proximal and distal open ends and having inherent tendency of coiling over a predetermined length at the distal end thereof, and a guide displaceable in the tube from the proximal end thereof for straightening said predetermined length in order that said length is straightened during the actual insertion into the stomach.

A catheter of this type is used for post-operative nutriment supply via the intestine in order to replace intravenous nutriment supply which is more difficult to administrate but above all costs 5 to 10 times more and also is associated with substantial complications. The catheter is positioned with the distal end thereof in the small intestine, preferably in the upper part of jejunum, in the manner described in EP 0 278 97. The catheter having said normally coiled predetermined length thereof straightened by the guide being pushed into said length is inserted at the distal end thereof into the stomach through the nose or the oral cavity via the gullet and the esophagus, or also percutaneously. At following nutriment supply in the normal manner during a predetermined period the catheter is advanced from the stomach into the small intestine by the movements of the stomach and the peristaltic movements of the intestine because the coiled length of the catheter will be processed by the stomach and the small intestine in the same manner as the surrounding nutriment. Thus, the catheter is self-feeding. Usually the coiled length of the catheter should be located in the upper part of jejunum, and when this position has been reached the catheter is fixed such that it cannot be further advanced into the small intestine. Once located the distal end of the catheter will be held anchored in jejunum by the coiled length engaging the inside corrugated surface of the intestine. The purpose is thus to provide the greatest possible friction between the catheter and the intestine wall.

JP-A-08098889 relates to a catheter to be inserted into the internal organs of the body and is of the prior art type having a weight at the distal end thereof in order that the catheter can more easily be inserted and located in the correct position in the organs. The catheter according to said publication in a distal end portion thereof forming a guide has a row of a number of polyhedral bodies having a specific weight of 1 or more and enclosed by an elastic film so that the catheter at the outside thereof forms unevenness in order to be advanced by peristaltic convulsions of the organs. The advantage of this embodiment of the catheter is said to be that the insertion of the catheter and change of the direction thereof will be facilitated the pain felt by the patient at the same time being reduced.

The catheter described in EP 0 278 937 has been found to well satisfy the purpose thereof in practice. The catheter does not differ essentially from conventional nasoenteric silicone tubes and, therefore, the costs for manufacturing such a catheter will not be much higher than those for manufacturing silicone tubes. It has been found that the catheter has advanced into the small intestine in 4 to 6 hours after the insertion. After the insertion it will be kept in the position thereof in the upper part of jejunum until it is to be removed usually after seven days or so. The risk of the catheter being returned to the stomach prematurely is small because said length of the catheter having a tendency to coil efficiently prevents dislocation by engaging the inside surface of the small intestine. In about 95% of the cases in which the catheter has been used it has attained the intended position in the small intestine and has maintained that position.

The advancement of the catheter can be stimulated by the supply of Metoclopramide or Erythromycin but not all patients can stand these agents due to side effects connected therewith.

The purpose of the present invention is to further improve the catheter according to EP 0 278 937 regarding self-advancement without supply of said agents while maintaining a safe and even improved retainment of the catheter in the predetermined position, and for this purpose the catheter according to the invention has obtained the characterizing features of claim 1.

BRIEF DESCRIPTION OF THE DRAWINGS

In order to explain the invention in more detail some embodiments thereof will be described reference being made to the accompanying drawing in which FIG. 1 is a side view of the catheter in one embodiment thereof with the tube straightened, FIG. 2 is a side view of the tube in FIG. 1 when the predetermined length of the tube having tendency to coil is in the coiled condition thereof, FIG. 3 is a fragmentary side view of the distal end position of the catheter in another embodiment thereof, and FIG. 4 is a view corresponding to FIG. 3 of the catheter in a third embodiment thereof.

DETAILED DESCRIPTION OF THE DISCLOSED EMBODIMENTS

Figure 5:
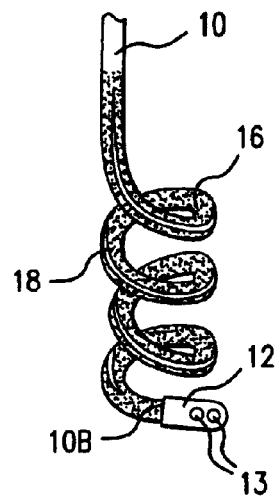
FIG. 5 is a view corresponding to FIG. 3 of the catheter in a fourth embodiment thereof.

The catheter according to the invention shown in FIGS. 1 and 2 comprises a resiliently flexible tube 10 preferably of plastic or rubber of medical quality such as polyurethane or silicone rubber, having a proximal end 10A and a distal end 10B. Preferably, the catheter has an outside diameter of 3.6 mm and an inside diameter of 1.5 mm but it can also have other dimensions. At the proximal end 10A the tube is provided with a guide socket 11 which communicates with the lumen of the tube, while the tube at the distal end 10B thereof is provided with a cap 12 which communicates with the lumen of the tube at one end and is closed at the other end and which has between the ends thereof radial side apertures 13. Socket 11 serves as a finger grip in order that the catheter can be more easily handled at the use thereof and can also be used for mounting the proximal end of the tube in a holder.

A flexible but unelastic and relatively rigid guide 14 of steel wire rope having substantially the same length as tube 10 is displaceably received in the tube and is provided at the proximal end thereof with a finger grip 15 at which the guide can be held at displacement thereof in the tube.

Adjacent the distal end the tube has a predetermined length with inherent (programmed) tendency of coiling to substantially the shape of a screw winding (memory function) as shown in FIG. 2. This property can be imparted to said predetermined length of the tube by a suitable choice of the material and by heating and curing while the tube length is coiled on a core. The coiled portion of the tube can comprise 1 to 5 turns and can have an outside diameter of about 40 mm. When the guide is pushed into said predetermined length of the tube this length is, however, substantially straightened as shown in FIG. 1, which implies that the guide has such a stiffness that there is required in order to bend the same a force which is greater than the coiling force of the tube.

Figure 6:
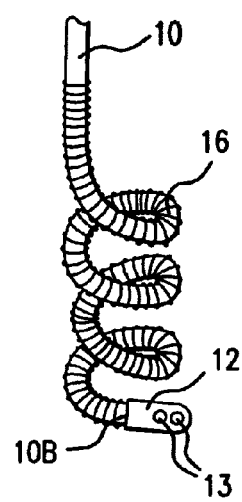
FIG. 6 is a view corresponding to FIG. 3 of the catheter in a fifth embodiment thereof.
Figure 7:
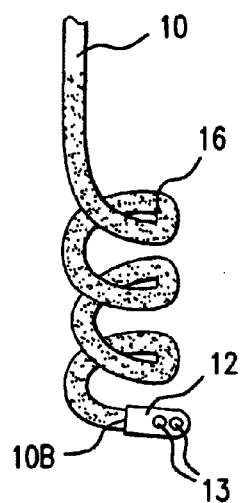
FIG. 7 is a view corresponding to FIG. 3 of the catheter in a sixth embodiment thereof.
Figure 8:
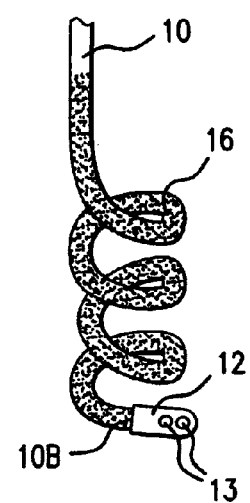
FIG. 8 is a view corresponding to FIG. 3 of the catheter in a seventh embodiment thereof.

At least the predetermined length of the tube at the distal end thereof having a tendency of coiling according to the invention is provided at the outside surface thereof with fimbriae-like short hairs as indicated at 16 in FIGS. 1 and 2 in order to stimulate the advancement of the catheter and more safely prevent dislocation thereof when it is in the predetermined position in the intestine by increased friction against the outside surface of the tube. However, this can also be achieved in another way, for example by providing on the tube a frosted, rough, or ribbed surface structure 16 as disclosed in FIGS. 5 to 8, respectively. Prior art electrostatic technique is well suited for providing an hairy surface on the outside of the tube. Said surface is made temporarily adhesive by applying some kind of glue, and short fibres of unitary length are applied on the surface in an electrostatic field, the fibres under the influence of the electrostatic field being held in a position in which they are directed radially outwards from the tube. This position will be maintained when the glue has set.

When the catheter is being used it is inserted into the stomach through the nose or through the oral cavity via the gullet and the esophagus, or percutaneously, with the catheter straightened by the guide 14 being pushed into the predetermined length with tendency of coiling, i.e. in the condition according to FIG. 1. The coiled portion being dimensioned as mentioned above the tube of FIG. 1 has an effective length which is 30 mm larger than the length in the condition according to FIG. 2. After insertion of the catheter into the stomach the guide is withdrawn a distance corresponding to said difference in effective length, i.e. about 30 mm, so that the tube will be free to coil in the stomach the tube then being advanced a corresponding distance in the stomach i.e. about 30 mm because the effective length of the catheter has been shortened by coiling. Then, the guide is withdrawn completely from the tube. The patient now ingests in the normal way through esophagus which of course implies that the tube is dimensioned so that there is a space for the passage of the food. The food in the stomach will surround the coiled length of the tube located therein, and this length of the tube will be processed in the same manner as the food the catheter being advanced in the small intestine by the movements of the stomach and then by the peristaltic movements of the small intestine. Thus, the catheter is self-advancing as described in EP 0 278 937. When the distal end of the catheter is located in the upper portion of jejunum the catheter will be fixed against further advancement for example by being taped against the body. The position of the distal end in the intestine can be controlled by X-ray, and for this purpose there can be embedded in the distal end for example in the cap a suitable contrast agent. The coiled length of the catheter maintains the catheter in the predetermined position in the intestine and thus functions as a dislocation lock. Due to said length being made hairy, frosted, rough or ribbed the "engagement" between the surrounding food and the catheter as well as the "engagement" between the inside surface of the intestine and the catheter will be increased without sliding of the catheter at the insertion being impeded as a consequence thereof. It is therefore expected that the catheter will be 100% safe with regard to the self-advancement as well as the retainment in the predetermined position by arranging the catheter in the manner proposed according to the invention.

Supply of a nutriment solution or medicaments or, alternatively, sampling takes place through the tube after the catheter being located in the predetermined position thereof.

In the embodiment according to FIG. 3 the tube is provided at the outside surface thereof with an axially extending radially projecting fin 17 which in the coiled length is located at the inside thereof, i.e. inside the screw shaped coil. Also in the embodiment according to FIG. 4 such a fin 18 is provided but in this case the fin is located at the outside of the coiled length. The fin should be thin and extendible and should be extremely soft and flexible and can consist of plastic or rubber. It may be made of the same material as the tube but this is not necessary. The fin may be formed at extrusion of the tube to extend not only over the predetermined length with tendency of coiling but over the total length of the tube. The fin can be combined with a hairy, frosted, rough or ribbed surface 16 on the tube, an on one and the same tube there may be provided two diametrically opposite fins so that the predetermined length with tendency of coiling in the coiled condition has a fin at the inside as well as the outside. On the inside the fin may be up to 10 mm wide while the fin at the outside should be no more than 1 to 2 mm. In a further conceivable embodiment of the invention the fin extends helically around the tube. The fin or fins provide a further strengthened "engagement" between the catheter and the food in the stomach, and if the fin is at the outside, FIG. 4, between the catheter and the inside surface of the intestine for promoting self-advancement and strengthening of the fixation of the catheter in the predetermined position, respectively.

The invention claimed is:

1. A catheter for providing a fluid connection with a small intestine, preferably for nutriment supply to said small intestine, comprising a tube (10) to be inserted into said small intestine via a stomach having proximal and distal open ends (10A, 10B) and having inherent tendency of coiling over a predetermined length at the distal end thereof, and a guide (14) displaceable in said tube from said proximal end thereof for straightening said predetermined length in order that it will be straightened during actual insertion in said stomach, wherein said tube (10) at least in said predetermined length has at least one of a hairy, frosted, rough, ribbed and finned outside surface (16).

2. The catheter as claimed in claim 1, wherein an axially extending radially projecting fin (17, 18) is provided on an outside surface of said tube (10) at least along said predetermined length with tendency of coiling.

3. The catheter as claimed in claim 2, wherein said fin (17) in a coiled portion formed by said predetermined length is located at an inside of said coiled portion.

4. The catheter as claimed in claim 2, wherein said fin (18) in a coiled portion formed by said predetermined length is located at an outside of said coiled portion.

5. The catheter as claimed in claim 2, wherein said fin (17, 18) extends helically around said tube (10).

6. The catheter as claimed in claim 2, wherein said fin (17, 18) is thin and extendible as well as soft and flexible.

7. The catheter as claimed in claim 1, wherein a coiled portion formed by said predetermined length comprises 1 to 5 turns and has an outside diameter up to 40 mm.

8. The catheter as claimed in claim 1, wherein a hairy surface (16) on said tube is provided as a velourized surface.

9. The catheter as claimed in claim 3, wherein said fin (17, 18) is thin and extendible as well as soft and flexible.

10. The catheter as claimed in claim 4, wherein said fin (17, 18) is thin and extendible as well as soft and flexible.

11. The catheter as claimed in claim 5, wherein said fin (17, 18) is thin and extendible as well as soft and flexible.

12. The catheter as claimed in claim 2, wherein a coiled portion formed by said predetermined length comprises 1 to 5 turns and has an outside diameter up to 40 mm.

13. The catheter as claimed in claim 3, wherein said coiled portion formed by said predetermined length comprises 1 to 5 turns and has an outside diameter up to 40 mm.

14. The catheter as claimed in claim 4, wherein said coiled portion formed by said predetermined length comprises 1 to 5 turns and has an outside diameter up to 40 mm.

15. The catheter as claimed in claim 5, wherein said coiled portion formed by said predetermined length comprises 1 to 5 turns and has an outside diameter up to 40 mm.

16. The catheter as claimed in claim 6, wherein said coiled portion formed by said predetermined length comprises 1 to 5 turns and has an outside diameter up to 40 mm.

17. The catheter as claimed in claim 2, wherein a hairy surface (16) on said tube is provided as a velourized surface.

18. The catheter as claimed in claim 3, wherein a hairy surface (16) on said tube is provided as a velourized surface.

19. The catheter as claimed in claim 4, wherein a hairy surface (16) on said tube is provided as a velourized surface.

20. The catheter as claimed in claim 5, wherein a hairy surface (16) on said tube is provided as a velourized surface.

21. The catheter as claimed in claim 6, wherein a hairy surface (16) on said tube is provided as a velourized surface.

22. The catheter as claimed in claim 7, wherein a hairy surface (16) on said tube is provided as a velourized surface.

* * * * *